United States Patent
Lenfers et al.

(10) Patent No.: US 6,774,236 B1
(45) Date of Patent: Aug. 10, 2004

(54) PROCESS FOR THE PREPARATION OF ENANTIOMERICALLY PURE CYCLOALKANO-INDOL -AND AZAINDOL -AND PYRIMIDO [1,2A] INDOLCARBOCYCLIC ACIDS AND THEIR ACTIVATED DERIVATIVES

(75) Inventors: Jan-Bernd Lenfers, Wuppertal (DE); Peter Fey, Wuppertal (DE); Paul Naab, Wuppertal (DE); Kai Van Laak, Cologne (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/307,980

(22) Filed: May 10, 1999

Related U.S. Application Data

(62) Division of application No. 08/829,566, filed on Mar. 31, 1997, now Pat. No. 5,952,498.

(30) Foreign Application Priority Data

Apr. 4, 1996 (DE) .......................................... 196 13 549

(51) Int. Cl.⁷ ..................... C07D 471/04; C07C 487/04; C07C 69/616; C07C 60/612
(52) U.S. Cl. ........................... 544/252; 560/8; 544/248; 544/252; 54/84; 54/85; 54/86; 54/87; 548/427
(58) Field of Search ............................. 560/8; 544/252

(56) References Cited

U.S. PATENT DOCUMENTS

| | | | |
|---|---|---|---|
| 4,970,215 A | 11/1990 | Mohrs et al. | |
| 5,459,156 A | * 10/1995 | Muller-Gliemann et al. | .......... 514/397 |
| 5,527,809 A | 6/1996 | Müller-Gliemann et al. | |
| 5,684,014 A | 11/1997 | Müller et al. | |
| 5,714,494 A | * 2/1998 | Connell et al. | ............. 514/263 |

FOREIGN PATENT DOCUMENTS

| | | |
|---|---|---|
| EP | 344519 | 11/1990 |
| EP | 513533 | 11/1992 |
| EP | 560163 | 9/1993 |
| EP | 610698 | 8/1994 |
| EP | 705831 | 4/1996 |

OTHER PUBLICATIONS

Connell et al. (CA 126:305588, abstract of EP 764,647), 1997.*

Masakazu Miyakado, et al. Agr. Biol. Chem., 39(1), 267–272; "Optical Resolution and Determination of Absolute Configurations of α–Isopropyl–4–substituted Phenylacetic Acids and Insecticidal Activities of Their 5–Benzyl–3–furylmethyl Esters" (1975).

* cited by examiner

*Primary Examiner*—Sabiha Qazi
(74) *Attorney, Agent, or Firm*—Norris McLaughlin & Marcus PA

(57) ABSTRACT

The invention relates to a process and intermediates for the preparation of enantiomerically pure cycloalkanoindolecarboxylic acids and azaindolecarboxylic acids and pyrimido [1,2a]indolecarboxylic acids and their activated derivatives, characterized in that the tolyl acetic acid is first esterified with a chiral alcohol, then diastereoselective substitution at α-carbon atoms is carried out and this product is halogenated in the tolyl group and then reacted with appropriate cycloalkanoindoles, cycloalkanoazaindoles or pyrimido[1, 2a]indoles. It is possible by this method to prepare specifically, in high purity, the enantiomerically pure carboxylic acids which are intermediates for valuable medicaments.

2 Claims, No Drawings

PROCESS FOR THE PREPARATION OF ENANTIOMERICALLY PURE CYCLOALKANO-INDOL -AND AZAINDOL -AND PYRIMIDO [1,2A] INDOLCARBOCYCLIC ACIDS AND THEIR ACTIVATED DERIVATIVES

This application is a division of Ser. No. 08/829,566 filed on Mar. 31, 1997, now Pat. No. 5,952,498, which claims priority to German Application 196 13 549.4 filed on Apr. 4, 1996.

The invention relates to a process for the preparation of enantiomerically pure cycloalkano-indolecarboxylic acids and azaindolecarboxylic acids and pyrimido[1,2a] indolecarboxylic acids and their activated derivatives, which represent important intermediates for the synthesis of anti-atherosclerotically active cycloalkanoindole derivatives and azaindole derivatives and pyrimido[1,2a]indole derivatives.

It is known that enantiomerically pure cycloalkano-indolecarboxylic acids and azaindole-carboxylic acids and their activated derivatives can be separated into the corresponding enantiomers by diastereomeric separation by conventional methods, for example by chromatography or fractional crystallization.

This process has a number of disadvantages: both the chromatographic diastereomeric separation and the fractional crystallization of the diastereomers are associated with high equipment requirements. In addition, in this case, generally 50% of the "wrong" diastereomer arises, which can no longer be recycled to the original preparation process. This 50% loss of yield considerably impairs the economic efficiency of a (large) industrial-scale process, quite apart from the fact that 50% of "by-product" must be disposed of. Furthermore, the customary chiral auxiliary reagents are generally very expensive even in small amounts and can then usually only be prepared via a complex synthetic pathway.

It has now been found that enantiomerically pure cycloalkano-indolecarboxylic acids and azaindolecarboxylic acids and pyrimido[1,2a]indole-carboxylic acids and their activated derivates of the general formula (I)

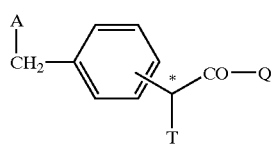

(I)

in which

A represents a radical of the formula

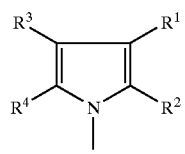

or

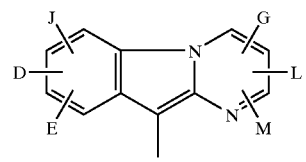

J, D, E, G, L and M are identical or different and denote hydrogen, halogen, trifluoromethyl, carboxyl, hydroxyl, linear or branched alkoxy or alkoxycarbonyl each having up to 6 carbon atoms, or linear or branched alkyl having up to 6 carbon atoms, which itself can be substituted by hydroxyl or by linear or branched alkoxy having up to 4 carbon atoms, in which $R^1$ and $R^2$, including the double bond linking them, together form a phenyl ring or pyridyl ring or a ring of the formula

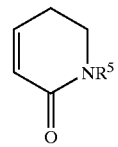

where $R^5$ denotes hydrogen or linear or branched alkyl having up to 4 carbon atoms, $R^3$ and $R^4$, including the double bond linking them, together form a phenyl ring or a 4- to 8-membered cycloalkene or oxocycloalkene radical, where all the ring systems listed under $R^1/R^2$ and $R^3/R^4$ are optionally up to trisubstituted identically or differently by halogen, trifluoromethyl, carboxyl, hydroxyl, by linear or branched alkoxy or alkoxycarbonyl each having up to 6 carbon atoms, or by linear or branched alkyl having up to 6 carbon atoms, which itself can be substituted by hydroxyl or by linear or branched alkoxy having up to 4 carbon atoms, T represents cycloalkyl having 4 to 12 carbon atoms, or represents linear or branched alkyl having up to 12 carbon atoms, Q represents hydroxyl or an activating radical, and their salts are obtained by firstly converting compounds of the general formula (II),

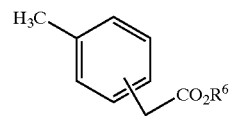

(II)

in which $R^6$ together with the oxygen atom represents a chiral alcohol radical, by means of compounds of the general formula (III)

T—Z (III)

in which

T has the meaning specified and

Z represents a typical leaving group, such as bromine, chlorine, iodine, mesyl, tosyl, or trifluoromethylsulphonyl, preferably iodine or bromine, n inert solvents in the presence of a base by diastereoselective alkylation into the enantiomerically pure compounds of the general formula (IV)

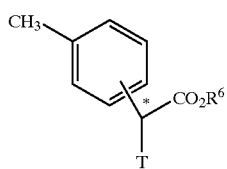
(IV)

in which
T and $R^6$ have the meaning specified,
then converting these, by halogenation, into the enantiomerically pure compounds of the general formula (V)

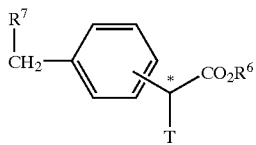
(V)

in which
T and $R^6$ have the meaning specified
and
$R^7$ represents halogen, such as chlorine, bromine, iodine, preferably bromine, reacting these in a further step with compounds of the general formula (VI)

A—H  (VI)

in which
$R^1$, $R^2$, $R^3$ and $R^4$ have the meaning specified,
to give the enantiomerically pure compounds of the general formula (VII)

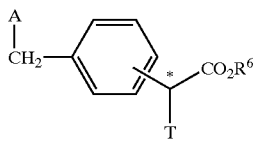
(VII)

in which
A, T and $R^6$ have the meaning specified,
and, in the case of compounds of the general formula (I) where Q=OH, carrying out a hydrolysis, and in the case where Q=activating radical, starting from the enantiomerically pure acids reacting with activating reagents.

These can be reacted in a further step with D- or L-phenylglycinol to give compounds of the general formula (VIII)

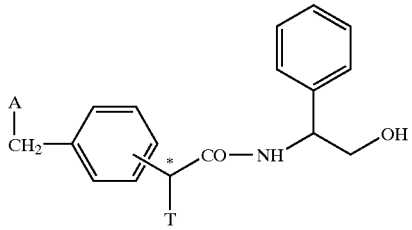
(VIII)

where these are in this case active compounds for medicaments.

The process according to the invention can be described by way of example by the following formula diagram:

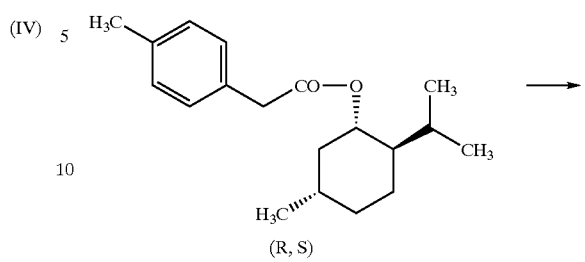

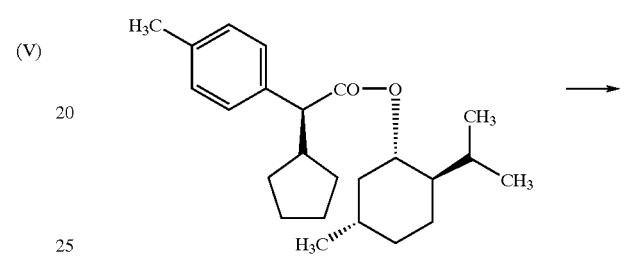

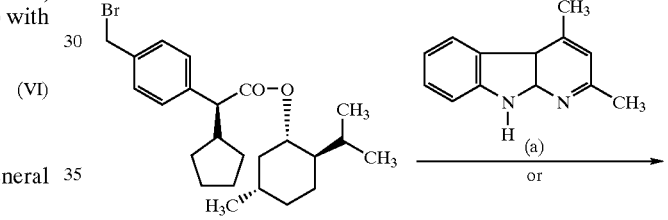

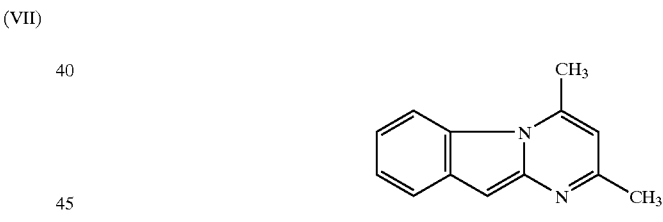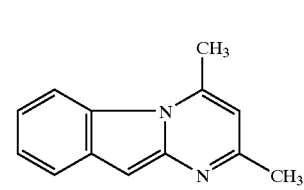

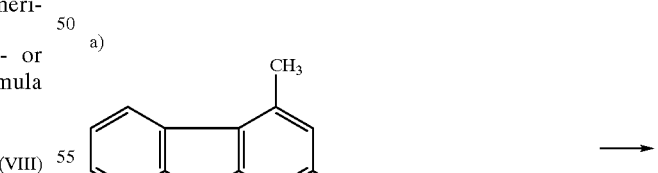

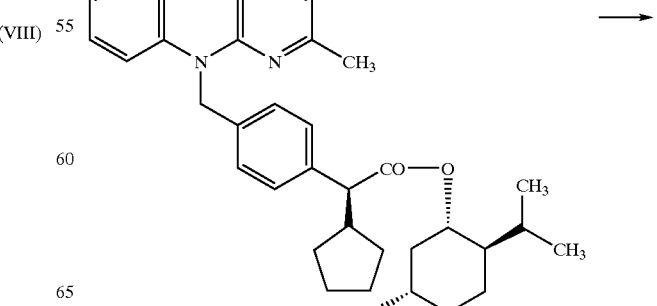

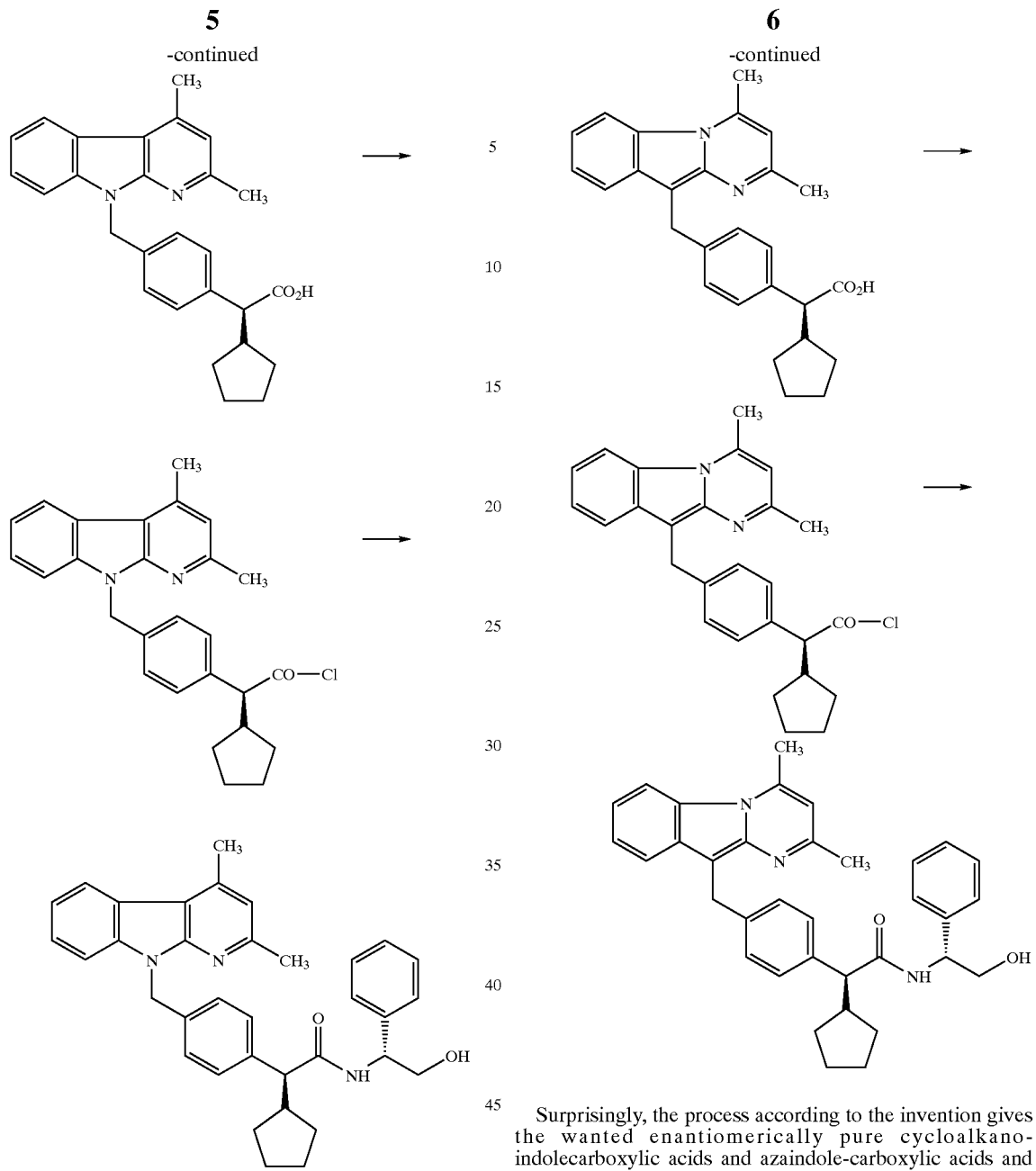
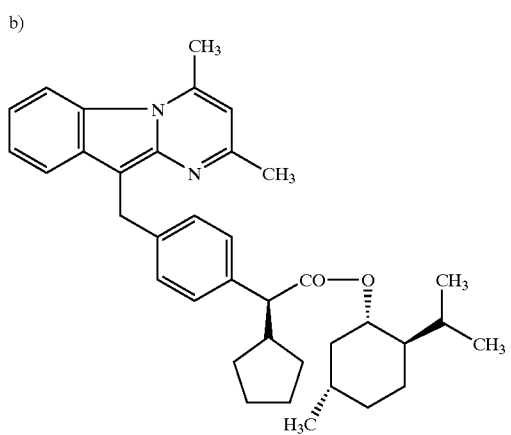

Surprisingly, the process according to the invention gives the wanted enantiomerically pure cycloalkano-indolecarboxylic acids and azaindole-carboxylic acids and pyrimido-indolecarboxylic acids and their activated derivatives without great equipment requirements in very good yields and high purity.

Depending on the configuration of the radical $R^6$ and stearic effects of the alkyl halide (II) used, the alkylation of the compound (II) proceeds in high yields and in a simple manner diastereoselectively for the first time. The compounds (IV) arise with high diastereomeric excess and crystallize out of the reaction mixture directly, as a result of which even the simple crystallization of crude products gives the compounds of the formula (IV) in diastereomerically pure form.

A further advantage of the process according to the invention is that, by suitable choice of the solvent and a base, the unwanted diastereomer can be epimerized to the desired diastereomer, which in turn crystallizes out directly. Thus, further (wanted) diastereomerically pure product can be produced from the mother liquors by repeated epimerization and crystallization. Direct addition of the mother liquors to the alkylation step can optimize the entire process in the form of a cyclic process.

A further advantage of the process according to the invention is that the halogenated compounds of the general formula (V) surprisingly react with the compounds of the general formula (VI) without racemization at the carbon atom in the 2 position to the carboxylic acid function, to give the compounds of the general formula (VII).

A further advantage of the process according to the invention is the racemization-free reaction at the carbon atom at the 2 position to the carboxylic acid function of the compounds of the general formula (I) where Q=activated radical, preferably chlorine, to give the compounds of the general formula (VIII).

Furthermore, it is a great advantage of the process according to the invention that the starting compounds are very readily accessible. They may be prepared in good yields from relatively simple building blocks with low equipment requirements. Furthermore, the process according to the invention enables amounts of known racemates of the compounds of the general formula (I) present to be converted into the corresponding enantiomers. The process according to the invention enables the preparation of the compounds according to the invention of the general formula (I) using few synthetic stages and in a considerably higher overall yield than by processes known from the prior art.

$R^6$, in the context of the above specified definition, represents a chiral alcohol radical, such as (+)- or (−)-menthyl, (+)- or (−)-bornyl, (+)- or (−)-isobornyl or (−)-8-phenylmenthyl. Preferably, $R^9$ represents (+)- or (−)-menthyl.

Activating radicals (Q), in the context of the invention, generally represent chloride, bromide, mesylate, tosylate or trifluoride. Preference is given to chloride. Preferably, by the process according to the invention, compounds of the general formula (I) are prepared, in which A represents a radical of the formula

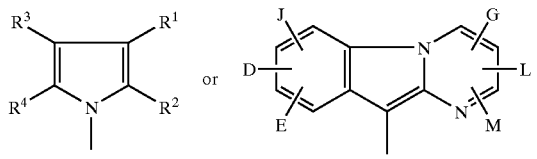

in which

J, D, E, G, L and M are identical or different and denote hydrogen, fluorine, chlorine, bromine trifluoromethyl, carboxyl, hydroxyl, linear or branched alkoxy or alkoxycarbonyl each having up to 4 carbon atoms, or linear or branched alkyl having up to 4 carbon atoms which itself can be substituted by hydroxyl or by linear or branched alkoxy having up to 3 carbon atoms, $R^1$ and $R^2$, including the double bond linking them, together form a phenyl ring or pyridyl ring or a ring of the formula

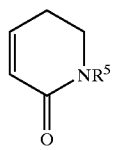

in which
$R^5$ denotes hydrogen or linear or branched alkyl having up to 3 carbon atoms,
$R^3$ and $R^4$, including the double bond linking them, together form a phenyl ring or a cyclopentene, cyclohexene, cycloheptene, cyclooctene, oxocyclopentene, oxocyclohexene, oxocycloheptene or oxocyclooctene radical,
where all ring systems, listed under $R^1/R^2$ and $R^3/R^4$ are optionally up to disubstituted identically or differently by fluorine, chlorine, bromine, trifluoromethyl, carboxyl, hydroxyl, by linear or branched alkoxy or alkoxycarbonyl each having up to 4 carbon atoms, or by linear or branched alkyl having up to 4 carbon atoms, which itself can be substituted by hydroxyl or by linear or branched alkoxy having up to 3 carbon atoms,
T represents cyclobutyl, cyclopentyl, cyclohexyl, cycloheptyl, cyclooctyl, or represents linear or branched alkyl having up to 10 carbon atoms,
Q represents hydroxyl or represents an activating radical, and their salts.

Particularly preferably, compounds of the general formula (I) are prepared by the process according to the invention in which A represents a radical of the formula

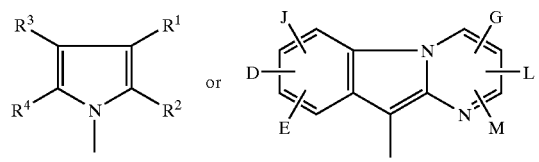

in which
J, D, E, G, L and M are identical or different and denote hydrogen, fluorine, chlorine, bromine, trifluoromethyl, carboxyl, hydroxyl, linear or branched alkoxy or alkoxycarbonyl each having up to 3 carbon atoms, or denote linear or branched alkyl having up to 3 carbon atoms,
$R^1$ and $R^2$, including the double bond linking them, together form a phenyl ring or pyridyl ring or a ring of the formula

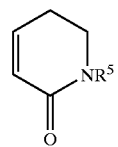

in which
$R^5$ denotes hydrogen or methyl,
$R^3$ and $R^4$, including the double bond linking them, together form a phenyl ring or a cyclopentene, cyclohexene, cycloheptene, cyclooctene, oxocyclopentene, oxocyclohexene, oxocycloheptene or oxocyclooctene radical,
where all ring systems listed under $R^1/R^2$ and $R^3/R^4$ are optionally up to disubstituted identically or differently by fluorine, chlorine, bromine, trifluoromethyl, carboxyl, hydroxyl, by linear or branched alkoxy or alkoxycarbonyl each having up to 3 carbon atoms or by linear or branched alkyl having up to 4 carbon atoms which itself can by substituted by hydroxyl, methoxy or ethoxy.
T represents cyclopentyl, cyclohexyl, cycloheptyl, cyclooctyl or linear or branched alkyl having up to 6 carbon atoms,
Q represents hydroxyl or an activating radical, and their salts.

Very particularly preferably, the compounds of the general formula (I), in which A represents a radical of the formula

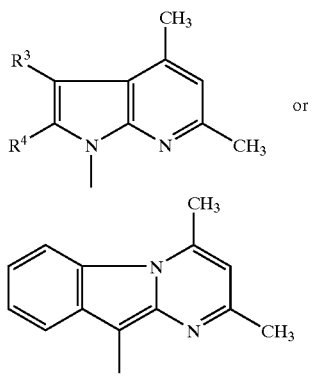

in which
R³ and R⁴=phenyl ring
and having the radical *CH—T—COQ in the parapo-
sition and Q=chlorine, and their salts,
are prepared by the above described process.

Suitable solvents for the alkylation of the compound of the general formula (II) are customary organic solvents which do not change under the reaction conditions. These preferably include ethers, such as diethyl ether, diisopropyl ether, tert-butyl methyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloro-methane, tetrachloromethane, dichloroethylene, trichloroethylene or chlorobenzene, or ethyl acetate, triethylamine, pyridine, dimethyl sulphoxide, dimethylformamide, N-methylpyrrolidone, hexamethylphosphoric triamide, acetonitrile, acetone or nitromethane, methanol or ethanol. It is equally possible to use mixtures of the said solvents. Preference is given to dimethylformamide.

The alkylation is carried out in the solvents listed above, if appropriate under a protective gas atmosphere, at temperatures of −20° C. to +100° C., preferably at −10° C. to +30° C., at atmospheric pressure.

Suitable bases for the diastereoselective alkylation are the customary basic compounds. These include alkali metal hydrides, such as sodium hydride, alkyli metal amides such as sodium amide, alkali metal alkoxides, such as sodium methoxide, sodium ethoxide, potassium methoxide, potassium ethoxide or potassium tert-butoxide, or organic amines, such as trialkylamines, e.g. triethylamine, or organolithium compounds, such as butyllithium or phenyllithium. Preference is given to potassium tert-butoxide.

In the diastereoselective alkylation, the base is used in an amount from 1 mol to 10 mol, preferably from 1.2 mol to 3 mol, based on 1 mol of the compounds of the general formula (II).

Suitable solvents for the halogenation of the compound for the general formula (IV) are customary solvents which do not change under the reaction conditions. These preferably include tetrachloromethane, chlorobenzene, dichlorobenzene, acetonitrile, acetic acid, sulphuric acid, nitrobenzene, 1,2-dichloroethane, dichloromethane, trichloromethane.

For the halogenation, customary halogenating agents are suitable, such as bromine, chlorine, NBS, NCS, dichlorodimethylhydantoin, dibromodimethylhydantoin, trichlorisocyanuric acid, chloramine-T.

Suitable free-radical starters are, for example, AIBN, peroxides, such as dibenzoyl peroxide, t-butyl hydroperoxide, dilauryl peroxide, t-butyl peroxide, butyl perbenzoate, di-t-butyl peroxalate, and photochemical methods.

The halogenation is carried out in the solvents listed above, if appropriate under a protective gas atmosphere, at temperatures of 20° C. to 180° C., if appropriate under pressure. Preferably, the halogenation is carried out at 70° C. to 130° C.

In the halogenation, the halogenating agent is used at 0.8 mol to 1.7 mol of active halogen, based on 1 mol of the compounds of the general formula (I).

Suitable solvents for the alkylation of the compound of the general formula (VI) are customary organic solvents which do not change under the reaction conditions. These preferably include ethers, such as diethyl ether, diisopropyl ether, tert-butyl methyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, tetrachloromethane, dichloroethylene, trichloroethylene or chlorobenzene, or ethyl acetate, triethylamine, pyridine, dimethyl sulphoxide, dimethylformamide, N-methylpyrrolidone, hexamethylphosphoric triamide, acetonitrile, acetone or nitromethane. It is equally possible to use mixtures of the said solvents. Preference is given to dimethylformamide, toluene and tetrahydrofuran.

The alkylation is carried out in the solvents listed above, if appropriate under a protective gas atmosphere, at temperatures of −20° C. to +100° C., preferably at −10° C. to +30° C., at atmospheric pressure.

Suitable bases are generally inorganic or organic bases. These preferably include alkali metal hydroxides, such as sodium hydroxide or potassium hydroxide, alkaline earth metal hydroxides, such as barium hydroxide, alkali metal carbonates and alkali metal hydrogen carbonates, such as sodium carbonate, sodium hydrogen carbonate or potassium carbonate, alkaline earth metal carbonates, such as calcium carbonate, or alkali metal alkoxides or alkaline earth metal alkoxides, such as sodium methoxide or potassium methoxide, sodium ethoxide or potassium ethoxide or potassium tert-butoxide, or organic amines (trialkyl($C_1$–$C_6$) amines), such as triethylamine, or heterocylcles, such as 1,4-diazabicyclo[2,2,2]octane (DABCO), 1,8-diazabicyclo[5,4,0]undec-7-ene (DBU), pyridine, diaminopyridine, methylpiperdine or morpholine. It is also possible to use alkali metals, such as sodium, or their hydrides, such as sodium hydride, as bases. Preference is given to sodium hydrogen carbonate, potassium carbonate and potassium tert-butoxide, DBU or DABCO.

In the alkylation, the base is used in an amount of 1 mol to 10 mol, preferably of 1.2 mol to 3 mol, based on 1 mol of the compounds of the general formula (II).

To eliminate the chiral radical $R^6$ in the compounds of the general formula (VII), the customary organic carboxylic acids are suitable, such as acetic acid, formic acid, trifluoroacetic acid, methanesulphonic acid, or inorganic acids, such as hydrobromic acid, hydrochloric acid or sulphuric acid or mixtures of the said acids. Preference is given to acetic acid, formic acid, hydrobromic acid and/or sulphuric acid. Very particular preference is given to the mixture acetic acid/sulphuric acid and also formic acid/hydrobromic acid and formic acid/sulphuric acid.

The acids or their mixtures are simultaneously employed as solvent and thus used in a great excess.

The elimination proceeds in a temperature range from 0° C. to +150° C., preferably from 40° C. to 100° C.

It can generally be carried out at atmospheric pressure, but optionally alternatively at superatmospheric pressure or reduced pressure (e.g. 0.5 to 3 bar).

After neutralization with bases in water or in one of the solvents listed above, in particular in a water/toluene, water/isopropanol, water/methanol or water/ethanol mixture, the acids are worked up by a customary method.

Suitable bases for the neutralization are alkali metal hydroxides, such as sodium hydroxide or potassium hydroxide. Preference is given to sodium hydroxide.

Suitable solvents for the activation of the compounds of the general formula (I) are customary organic solvents which do not change under the reaction conditions. These preferably include ethers, such as diethyl ether, diisopropyl ether, tert-butyl methyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, tetrachloromethane, dichloroethylene, trichloroethylene or chlorobenzene, or ethyl acetate, triethylamine, pyridine, dimethyl sulphoxide, dimethylformamide, acetonitrile, acetone or nitromethane. It is equally possible to use mixtures of the said solvents. Preference is given to dimethylformamide, toluene and dichloromethane.

For the activation, conventional activation agents are suitable, for example oxalyl chloride, phosphorus trichloride, phosphorus pentachloride, trichloroisocyanuric acid, thionyl chloride, phosphorus tribromide, phosphorus pentabromide, mesyl chloride, tosyl chloride, phosgene, trifluoromethanesulphonyl chloride, sulphuryl chloride. Preference is given to thionyl chloride, oxalyl chloride and phosgene.

The activation is carried out in the solvents listed above, if appropriate under a protective gas atmosphere, at temperatures of −20° C. to 120° C., optionally under pressure. Preferably, the activation is carried out at −20° C. to 80°.

In the activation, the activation reagent is used in an amount of 1 mol to 10 mol, based on 1 mol of the compound of the general formula (I), or is optionally employed as solvent.

The activation is optionally performed with the addition of bases, such as organic amines (trialkyl($C_1$–$C_6$)amines), such as triethylamine, or heterocycles, such as 1,4-diazabicyclo[2,2,2]octane (DABCO), 1,8-diazabicyclo[5,4,0]undec-7-ene (DBU), pyridine, diaminopyridine, methylpiperidine or morpholine. If appropriate, the activated derivatives can be prepared starting from carboxylic salts of alkali metals and alkaline earth metals by reaction with, e.g., oxalyl chloride.

The compounds of the general formula (II),

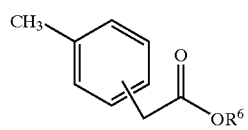

(II)

in which $R^6$ represents a chiral alcohol radical, are obtained by esterifying compounds of the general formula (IX)

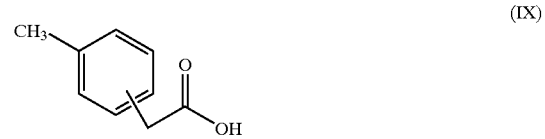

(IX)

with chiral alcohols according to processes disclosed in the literature.

The compounds of the general formula (IX) are known per se or can be prepared by customary methods.

The enantiomerically pure compounds of the general formula (I) in which Q represents tert-butoxy are novel and can be prepared by first converting racemic carboxylic acids of the general formula (X)

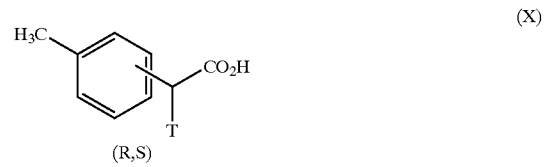

(X)

in which

T has the meaning specified above, by reaction with (R)- or (S)-phenylethylamine in inert solvents and subsequent crystallization of the phenethylammonium salts and subsequent hydrolysis of the salts, into the enantiomerically pure compounds of the general formula (XI)

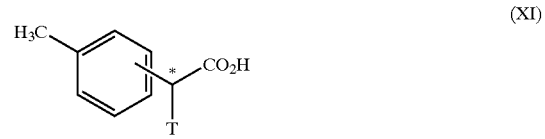

(XI)

in which

T has the meaning specified above, converting these in a further step with isobutene, in inert solvents and in the presence of acids, into the enantiomerically pure esters (XII)

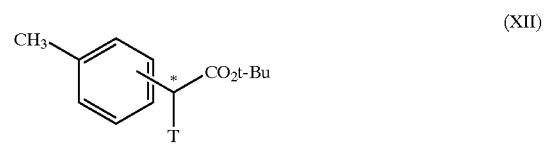

(XII)

in which

T has the meaning specified above, then converting the esters (XII) by halogenation into the enantiomerically pure compounds of the general formula (XIII)

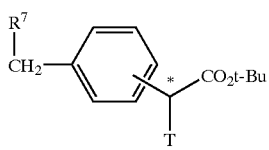 (XIII)

in which

T has the meaning specified above and

R⁷ represents a typical leaving group, such as chlorine, bromine, iodine, tosylate or mesylate, preferably bromine, in a further step, by reaction with compounds of the general formula (VI)

A—H  (VI)

in which

A has the meaning specified above, preparing the enantiomerically pure compounds of the general formula (I)

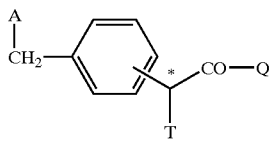 (I)

in which

A and T have the meaning specified above and

Q represents tert-butyl, and in the case of the compounds of the general formula (I) where Q=OH, carrying out a hydrolysis.

Tert-butyl esters are generally saponified with acids, for example hydrochloric acid or trifluoroacetic acid, in the presence of one of the above specified solvents and/or water or their mixtures, preferably with dioxane or tetrahydrofuran.

The compounds of the general formula (X) are prepared from the corresponding esters disclosed in the literature by hydrolysis according to methods disclosed in the literature.

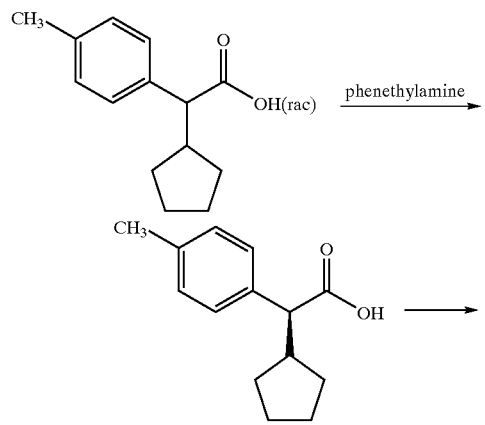

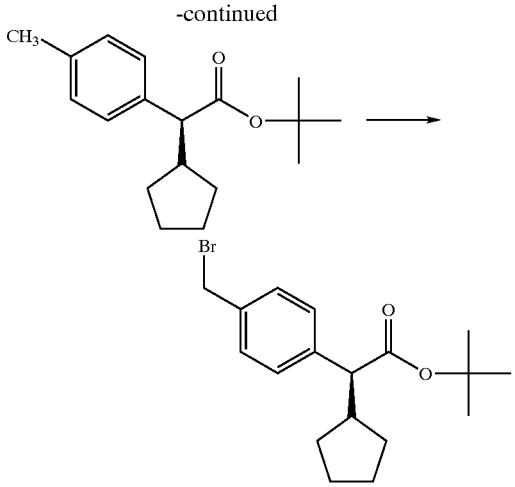

EXAMPLE I

2(R/S)-2-Cyclopentyl-2-(4-methylphenyl)-acetic acid

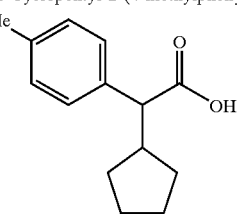

2.0 kg (7.2 mol) of tert-butyl 2(R,S)-2-cyclopentyl-2-(4-methylphenyl)-acetate are dissolved in 4 l of dioxane in a 40 l agitated vessel fitted with an attached washing tower. After addition of 4.5 l of concentrated hydrochloric acid, the mixture is stirred at 50° C. to complete conversion (3 h). The reaction mixture is admixed with ice and adjusted to pH=12 with concentrated sodium hydroxide solution. After addition of water to complete solution of the solids, the mixture is washed with acetic acid, the organic phase is washed with dilute sodium hydroxide solution and the combined aqueous phases are adjusted to pH=1, with cooling, with concentrated hydrochloric acid. The mixture is washed twice with ethyl acetate, dried over sodium sulphate and concentrated.

Yield: 1.27 kg; 81% of theory. Melting point: 92° C. $R_f$=0.20 (petroleum ether:ethylacetate=4:1) ¹H-NMR (CDCl₃, 200 MHz, TMS): δ=0.98 (m, 1H); 1.20–1.71 (m, 6H); 1.82–2.05 (m, 1H); 2.31 (s, 3H); 2.52 (m, 1H); 3.21 (d, 1H); 7.10 (m, 2H); 7.21 (m, 2H); 11.90 (br, s, 1H) ppm.

EXAMPLE II (S)-2-Cyclopentyl-2-(4-methylphenyl)-acetic acid

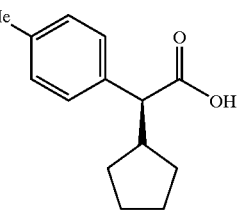

2.4 l of THF and 129.7 g (1.28 mol) of triethylamine are added, with stirring, to a suspension of 560 g (2.57 mol) of the compound from Example I in 4.8 l of water. The resulting solution is heated to 60° C., 155.4 g (1.28 mmol) of (S)-(−)-phenethylamine are added and the resulting suspension is stirred for 2 h at 60° C. The reaction mixture is cooled to 20° C., the precipitate is filtered off by suction, washed with 2.4 l of water/FHF (2:1) and dried under reduced pressure.

Yield: 360 g of phenethylammonium salt; 41.3% of theory. 745 g (2.2 mol) of phenethylammonium salt are suspended in 3 l of water, acidified (pH=1) with dilute hydrochloric acid (1:1) and stirred for 30 minutes. The oily suspension is washed 3 times, each time with 1 l of dichloromethane, the combined organic phases are now washed with water, dried over sodium sulphate and concentrated, the residue crystallizing out.

Yield: 475 g; 37.3% of theory, based on racemate of Example No. I ee: 96.3% (HPLC) Melting point: 66° C.

By crystallization of the phenethylammonium salt from THF, as described above, the pure enantiomer is obtained:

ee: >99.5% (HPLC) Specific rotation: $[\alpha]_D^{20}$=+59.55 (ethanol/c=0.85)

The HPLC method for determination of the ee value is as follows:

| Column: | Chiracel OJ (Daicel) |
|---|---|
| Particle size: | 10μ |
| Packing: | 250 × 2 mm (Grom) |
| Mobile phase: | n-heptane: 2-propanol = 97:3 |
| Flow rate: | 0.2 ml/min |
| Inlet pressure: | 22 bar |

EXAMPLE III

Tert-butyl (S)-2-cyclopentyl-2-(4-methylphenyl)-acetate

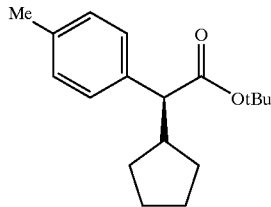

6 ml of concentrated sulphuric acid are added to a solution of 465 g (2.13 mol) of the compound from Example II in 1.4 l of dichloromethane, a temperature of approximately 10° C. being established. 550 ml (5 mol) of isobutene are condensed in a Dewar flask and added in one portion to the starting material solution. The reaction mixture is stirred over night. To complete the reaction, a further 6 ml of concentrated sulphuric acid and 500 ml of isobutene are added and stirred over night. After addition of 40 g of potassium carbonate, the mixture is stirred for 3 h. and then 2 l of water are added, vigorous gas development initially occurring. The mixture is washed three times, each time with 2 l of dichloromethane, the combined organic phases are washed with 5 l of sodium chloride solution, dried over sodium sulphate and concentrated to give an oil which slowly crystallizes.

Yield: 480 g; 82% of theory Melting point: 45° C. $R_f$=0.90 (toluene:ethyl acetate=8:2)

EXAMPLE IV

Tert-butyl (S)-2-(4-bromomethylphenyl)-2-cyclopentyl-acetate

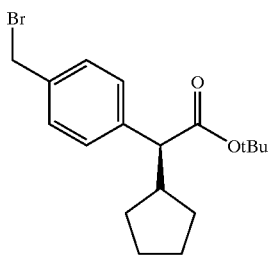

In a 10 l flask, 480 g (1.75 mol) of the compound from Example III are dissolved under reflux in 3.4 l of tetrachloromethane and 70 g of a total amount of 311 g (1.75 mol) of NBS and 14 g (0.085 mol) of AIBN are added. The reaction begins after refluxing for approximately 1 h; after it decays, further NBS is added in 50 g portions. After refluxing for 5 h and subsequent standing over night at room temperature, for the work-up, the mixture is cooled to 0° C., the succinimide is filtered off with suction and washed with 600 ml of tetrachloromethane. The combined filtrates are concentrated and residual solvent is removed under reduced pressure to constant weight.

Crude yield: 570 g; approximately 100% of theory HPLC: 68.8% (15.5% starting material, 10.1% dibromo compound) The pure substance is obtained by column chromatography $R_f$=0.42 (petroleum ether, ethyl acetate=20/1) $^1$H-NMR (CDCl$_3$, 200 MHz, TMS): δ=0.98 (m, 1H); 1.22–1.71 (m, 6H); 1.40 (s, 9H); 1.90 (m, 1H); 2.47 (m, 1H); 3.16 (d, 1H); 4.49 (s, 2H); 7.32 (m, 4H) ppm.

EXAMPLE V (L)-menthyl 2-(4-tolyl)-acetate

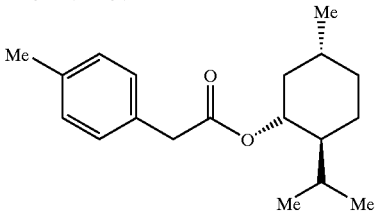

3.15 kg of p-tolylacetic acid and 9.45 l of toluene are introduced. 3.115 kg of L-menthol and 21.4 ml of methanesulphonic acid are added with stirring and cooling. The mixture is then heated to reflux temperature and the corresponding amount of water is separated off in the course of 16 to 20 hours via a water separator. After cooling to room temperature, the mixture is stirred once with 4.41 l of saturated sodium hydrogen carbonate solution and twice, each time with 4.41 l of water. The organic phase is freed from solvent and gives 5.725 kg of the wanted compound (GC 99.9%, retention time 19.49 min). $^1$H-NMR (CDCl$_3$, ppm): 7.05–7.15 (4H, m); 4.55 (1H, txd); 3.5 (2H, s); 2.8 (3H, s); 0.65 (3H, s).

EXAMPLE VI (L)-menthyl 2-(S)-2-cyclopentyl -2-(4-tolyl)-acetate

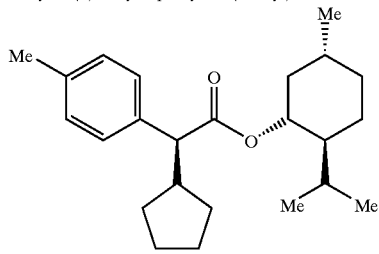

1.575 kg of potassium tert-butoxide are dissolved in 3.75 l of DMF at room temperature. The mixture is cooled to 10° C. and, in the course of 45 minutes, 2.678 kg of the compound from Example V are run in at this temperature and rinsed with 0.375 l of DMF. Then, with full cooling, 1.658 kg of cyclopentyl bromide are pumped in in the course of 1 to 2 hours. The suspension is further stirred for 1 hour without cooling and then cooled to −7° C. When −10° C. is reached, the mixture is seeded with the correct diastereomer and then further cooled to −7° C. When −7° C. is reached, the mixture is further stirred for 3 to 4 hours at this temperature. The reaction suspension is worked up by introducing it into a mixture of 1.5 kg of ice and 6 kg of water. The batch is then stirred over night at 0 to 2° C. It is worked up by filtering off the suspension with suction and washing the crystals with a total of 2.5 of water. The crystals are dried at 45° C. in a vacuum drying cabinet. 3.289 kg of an 85 to 15 diastereomer mixture are obtained.

4.345 kg of a mixture prepared as described above are dissolved in 21.75 l at 30 to 35° C. After seeding with the correct diastereomer and cooling to room temperature, the mixture is stirred over night and cooled the next morning to 0 to 5° C. After 1 to 2 hours at this temperature, the crystals are filtered off with suction, dried or recrystallized. By repeating the methanol crystallization once or twice, material having a diastereomeric purity ≧99.5% can be prepared (GC retention time 22.61 min).

The yield of diastereomerically pure title compound is 65–70% over the stages cyclopentylation and pure crystallization and can be increased to 75–80% by recrystallization and by epimerization of the mother liquors with potassium tert-butoxide in DMF and recrystallization of the crude diastereomer mixture. $^{13}$C-NMR (CDCl$_3$, CH-signal, ppm): 128.90; 128.92; 73.96; 57.85; 46.92; 42.13; 31.28; 25.96.

EXAMPLE VII (L)-menthyl 2-(S)-2-(4-bromomethyl-phenyl)-2-cyclopentyl-acetate

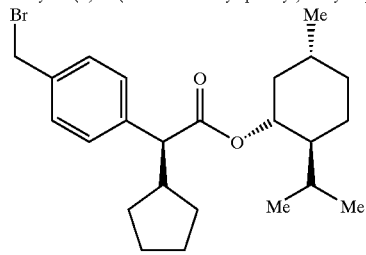

1.40 kg of the compound from Example VI are heated to 80° C. in 13.74 l of chlorobenzene. 0.618 kg of 1,3-dibromo-5,5-dimethylhydantoin are then added and the mixture is further heated to 85° C. 20.4 g of AIBN are then added at this temperature to start the reaction. The temperature increases after the start of the reaction to 90 to 105° C., but then decreases again to about 85° C. The mixture is allowed to react further for a total of 2 hours. The vessel contents are then cooled to room temperature and further stirred for one hour. The precipitated crystals are filtered off with suction and the filtrate is freed from solvent. The remaining oil is 61.2% pure according to HPLC analysis (retention time: 14.68 min). 1.69 kg are obtained. The mixture can be used in the crude state in the following alkylations. Chromatography and subsequent crystallization give a white powder at melting point 57–58° C. having the correct CH analysis.

$^1$H-NMR (CDCl$_3$, ppm): 7.3 (4H, s); 4.65 (1H, txd); 4.45 (2H, s); 3.35 (1H, d); 0.65 (3H, d).

EXAMPLE VIII (L)-menthyl 2(S)-2-cyclopentyl-2[4-(2,4-dimethyl-α-carbolin-9- yl) methyl]phenyl-acetate

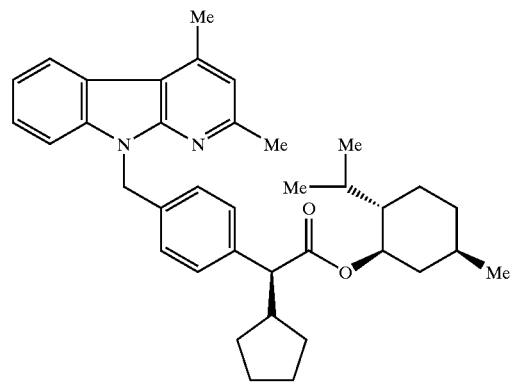

The reaction is carried out under a nitrogen atmosphere. 480 g (2.44 mol) of carboline are suspended in 4.13 l of dimethylformamide and 287.7 g of potassium tert-butoxide dissolved in 1 l dimethylformamide are added, with stirring. The reaction solution heats to 30° C. After 30 min, the batch is cooled to 20° C. 1.707 kg (2.69 mol) of 69% strength menthyl ester bromide, dissolved in 1.56 l of dimethylformamide, are then added dropwise in such a manner that the internal temperature does not exceed 35° C. After a further 15 min of reaction time, the reaction solution is poured into a mixture of 1.8 l of 10% strength sodium chloride solution and 13 l of ethyl acetate. After 20 min, with stirring, the ethyl acetate phase is separated off and extracted twice, each time with 3 of 10% strength sodium chloride solution. After drying the organic phase over sodium sulphate, ethyl acetate is distilled off under reduced pressure at approximately 40° C. The syrupy residue is taken up in 4.4 l of methanol and stirred for 30 min under reflux at room temperature for 12 h. The precipitated crystals are filtered off with suction, washed with methanol and dried under reduced pressure at 40° C.

Yield: 947 g(70.6% of theory) Melting point: 142° C.

EXAMPLE IX 2-(S)-2-cyclopentyl-2-[4-(2,4-dimethyl-α-carbolin-9-yl)-methyl]phenylacetic acid

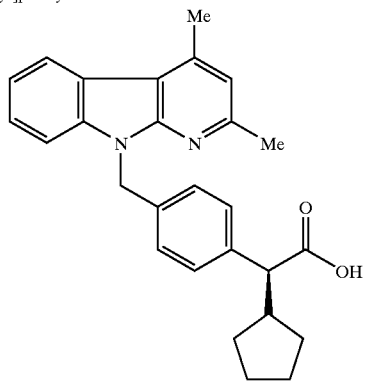

947 g (1.72 mol) of the compound from Example VIII are admixed with 2.4 l of formic acid. 1.21 l of aqueous hydrobromic acid (48% strength) are added dropwise with stirring. The resulting suspension is stirred for 6 hours at 95–98° C. and then cooled to room temperature. The reaction solution is admixed with 1.6 l of isopropanol and 3.2 l of water, with stirring. A pH of 5 is established with 45% strength sodium hydroxide solution, with gentle cooling (consumption of sodium hydroxide solution: 5.2 kg). The precipitate is filtered off with suction, washed twice with 5.7 l of water and sucked dry. The water-moist product is then stirred in 2.6 l of isopropanol for 2 hours at room temperature. The crystals are filtered off with suction, washed with 2.8 l of isopropanol and dried under reduced pressure at 60° C.

Yield: 574 g (81% of theory) Melting point: 197–199° C.

EXAMPLE X

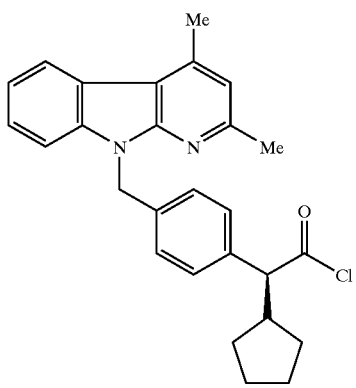

A suspension of 350 g (0.85 mol) of the compound from Example IX in 3 l of methylene chloride is heated to reflux, with stirring. In the course of 1 h, 95 ml (155 g, 13 mol) of thionyl chloride are added dropwise and the mixture is stirred for a further 2 h at reflux temperature. The reaction solution is then cooled to room temperature, concentrated at 25–30° C. under reduced pressure until the beginning of crystallization and admixed with 2.5 l of toluene. At a temperature of 30–40° C., a further 2.3 l of solvent are distilled off under reduced pressure. After cooling to approximately 20° C., 1.2 l of toluene are added to the batch. The suspension is cooled to 0–5° C., stirred for 1 h at this temperature, filtered with suction, washed with 1.4 l of toluene and sucked dry. The toluene-moist product is reacted without further characterization.

EXAMPLE XI

N-[2-(S)-2-cyclopentyl-2-[4-(2,4-dimethyl-α-carbolin-9-yl)-methyl]phenylacetyl]-(R)-phenylglycinol

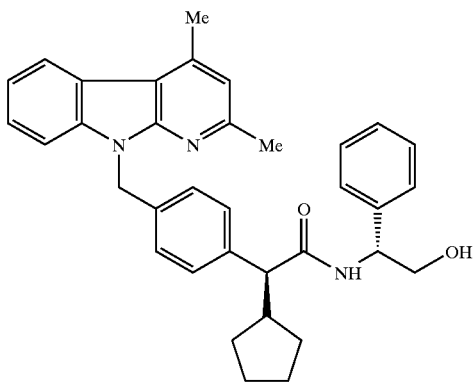

458 g of toluene-moist acid chloride, 125 g of R-phenylglycinol and 8.5 liters of toluene are introduced into a 20 l flange flask and stirred. Beginning at 20° C., 235 ml (171 g, 1.7 mol) of triethylamine are added dropwise in the course of 15 min. The mixture is then stirred for 1 hour at 60–65° C., cooled to room temperature and stirred at this temperature for 8 h. The precipitated crystals are filtered off with suction, washed with toluene and sucked dry. After the toluene-moist crystals have been heated to boiling in 11 liters of ethanol for 15 min, 7.5 liters of ethanol are distilled off and then 8 liters of water at boiling heat are added. The mixture is stirred for a further 15 min at reflux temperature. The flask contents are cooled to 20° C. The crystals are filtered off with suction, washed 3 times, each time with 3.5 liters of water, and dried under reduced pressure at 80° C. The dried crude product is recrystallized from approximately 4 liters of methyl ethyl ketone.

Yield: 383 g (85% of theory) Melting point: 221° C.

EXAMPLE XII (L)-menthyl 2-(S)-2-cyclopentyl -2-[4-(2,4-dimethyl-pyrimido[1,2-a]-indol-9-yl)-methyl)phenyl]acetate

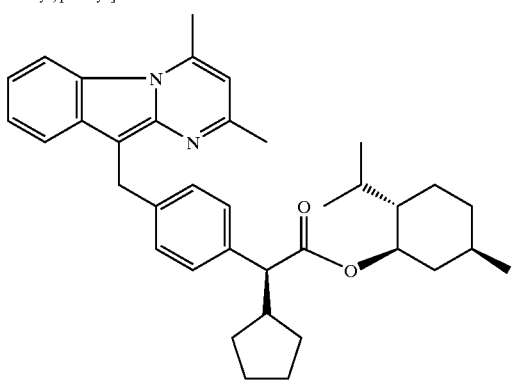

41.9 g (0.2 mol) of 2,4-dimethyl-pyrimido[1,2-a]indole and 33.6 g of sodium hydrogen carbonate are introduced into 300 ml of dimethyl-formamide. The mixture is heated to 120° C. and a solution of 128.1 g (0.2 mol, 68% strength) of the compound from Example XII (bromide) in 135 ml of dimethylformamide is added dropwise at 30–70° C. in the course of 10 min. The mixture is stirred for 40 min at 120° C. and the reaction mixture is poured into 2.2 l of semi-concentrated sodium chloride solution at room temperature. After extraction with 2.2 l of ethyl acetate, the organic phase is washed 3 times with semi-concentrated sodium chloride solution, dried over sodium sulphate and concentrated at 50° C.

Yield: 165.4 g (70.4% of theory) HPLC: 46.9%

EXAMPLE XIII

Menthyl-2-(S)-2-cyclopentyl-2-[4-(2,4-dimethyl-pyrimido[1,2-a]-indol-9-yl)-methyl)phenyl]acetate hydrochloride

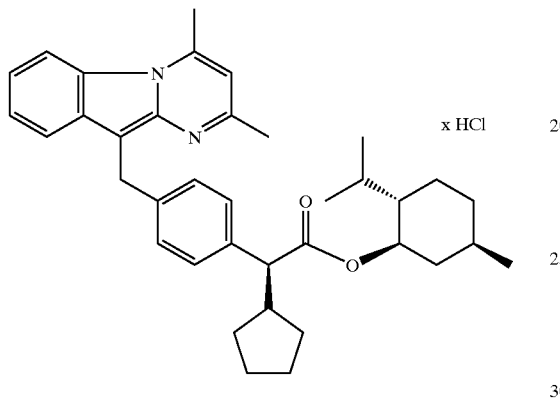

165.4 g (0.14 mol) of the crude product from Example XII are dissolved in 1.6 l of acetone at 50° C. In the course of 10 min, 80 ml (0.48 mol) of semi-concentrated hydrochloric acid are added dropwise at 15 to 20° C. and the mixture is stirred for 2 h at approximately 10° C. The precipitated solid is filtered off with suction, washed with a sparing amount of acetone and dried at 50° C. under reduced pressure.

Yield: 60.7 g (39.3% of theory, based on pyrimidoindole) HPLC: 76.1%

EXAMPLE XIV 2-(S)-2-cyclopentyl-2-[4-(2,4-dimethyl-pyrimido[1,2-a]-indol-9-yl)-methyl)phenyl]acetic acid

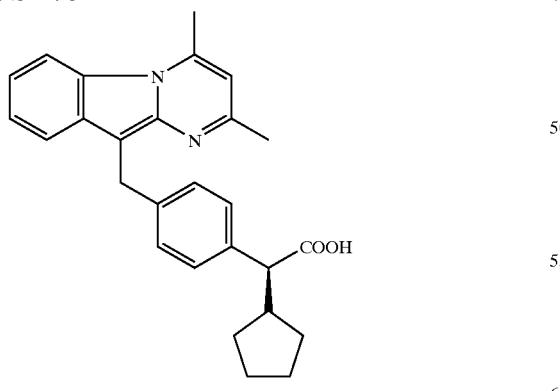

60.7 g (0.10 mol 76.1% pure) of the compound from Example XII are dissolved in 146 ml of formic acid and 43 ml of 48% strength hydrobromic acid and stirred for 6 h under reflux (109° C.), the reaction mixture foaming vigorously initially. At room temperature, 94 ml of isopropanol and 187 ml of water are added and, with cooling, in the course of 1 h, the mixture is adjusted to pH 5 by addition of 190 ml of concentrated sodium hydroxide solution. The mixture is stirred for 2 h, the solids are filtered off with suction and washed three times with isopropanol, each time with 100 ml, and three times with water, each time with 100 ml. The residue is stirred for 1 h with 310 ml of isopropanol, filtered off with suction, washed with a sparing amount of isopropanol and dried under reduced pressure at 50° C.

Yield: 36.9 g (approximately 100% of theory) HPLC:92.1%

EXAMPLE XV 2-(S)-2-cyclopentyl-2-[4-(2,4-dimethyl-pyrimido[1,2-a]indol-9-yl)-methyl)phenyl]acetyl chloride

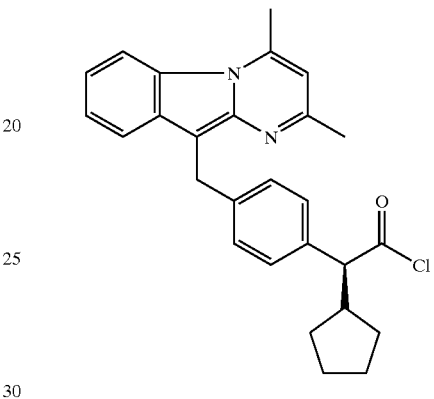

10 ml (0.14 mol) of thionyl chloride are added dropwise in the course of 10 min at 39° C. to a solution of 37.1 g (0.09 mol) of the compound from Example XIV in 306 ml of dichloromethane, and the resulting gases are passed into a scrubbing tower. The mixture is stirred under reflux for 2 h and volatile portions are distilled off under reduced pressure at 40° C. bath temperature. The remaining thick suspension is admixed with 270 ml of toluene, concentrated under reduced pressure at 50° C. and the residue is stirred with 270 ml of toluene at room temperature for 2 h. The product is filtered off with suction, washed with a sparing amount of toluene and dried under reduced pressure.

Yield: 47 g (toluene-moist)

EXAMPLE XVI

N-[2-(S)-2-cyclopentyl-2-[4-(2,4-dimethyl-pyrimido[1,2-a]-indol-9-yl)-methyl]phenylacetyl]-(R)-phenylglycinol

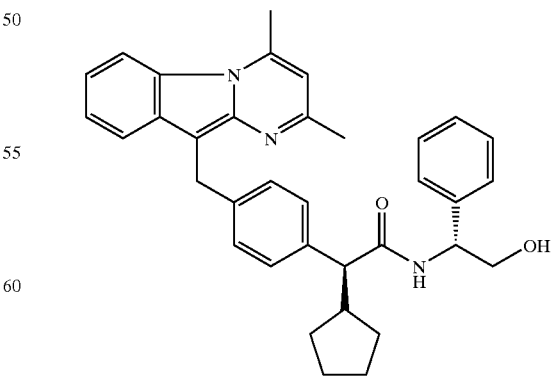

The toluene-moist crude product (47 g, approximately 0.08 mol) from Example XV is suspended in 810 ml of toluene. 11.8 g (0.086 mol) of D-phenylglycinol and 23 ml (0.166 mol) of triethylamine are added and the mixture is stirred at 61 to 63° C. for 1 h. The solids are filtered off with suction at room temperature and stirred for 2 h with 500 ml of water and 50 ml of saturated sodium hydrogen carbonate solution. The solids are filtered off with suction, washed with 150 ml of water and dried at 50° C. under reduced pressure.

The crude product (32.3 g) is dissolved in 1 l of methyl ethyl ketone at boiling heat, filtered off hot with suction from insoluble portions, the filtrate is concentrated to approximately 200 ml and cooled with an ice bath. The product which has crystallized out is filtered off with suction, dried at 50° C. under reduced pressure, dissolved in 2 l of methanol at boiling heat, filtered off hot with suction and concentrated to 150 ml. The product which has precipitated out at room temperature is filtered off with suction, washed with 150 ml of methanol and dried at 50° C. under reduced pressure.

Yield: 14.9 g (34.6% of theory) HPLC: 99.9% Melting point: 195–200° C.

What is claimed is:

1. A compound of the formula (IV)

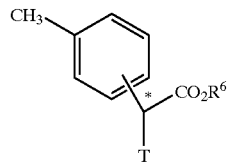

(IV)

in which

T represents a cycloalkyl having 4 to 12 carbon atoms or represents linear or branched alkyl having up to 12 carbon atoms and $R^6$ represents the D- or L-menthyl radical or tert-butyl, with the exception of the compound having T=isopropyl and the compound.

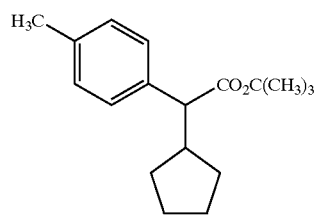

2. A compound of the formula (V)

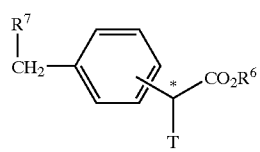

(V)

in which $R^6$ represents the D- or L-menthyl radical or represents the tert-butyl radical, T represents a cycloalkyl having 4 to 12 carbon atoms or represents linear or branched alkyl having up to 12 carbon atoms, and $R^7$ represents bromine expect for the compound.

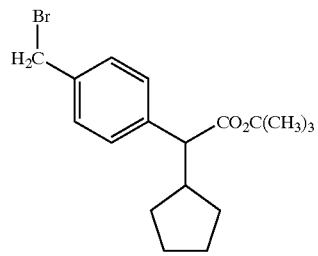

* * * * *